(12) United States Patent
Sutherland

(10) Patent No.: US 10,828,434 B2
(45) Date of Patent: *Nov. 10, 2020

(54) COMPLIANCE MONITOR FOR A MEDICAMENT INHALER

(71) Applicant: Adherium (NZ) Limited, Auckland (NZ)

(72) Inventor: Garth Campbell Sutherland, Auckland (NZ)

(73) Assignee: ADHERIUM (NZ) LIMITED, Auckland (NZ)

( * ) Notice: Subject to any disclaimer, the term of this patent is extended or adjusted under 35 U.S.C. 154(b) by 1044 days.

This patent is subject to a terminal disclaimer.

(21) Appl. No.: 14/915,612

(22) PCT Filed: Aug. 29, 2014

(86) PCT No.: PCT/NZ2014/000184
§ 371 (c)(1),
(2) Date: Feb. 29, 2016

(87) PCT Pub. No.: WO2015/030610
PCT Pub. Date: Mar. 5, 2015

(65) Prior Publication Data
US 2016/0228657 A1    Aug. 11, 2016

(30) Foreign Application Priority Data

Aug. 30, 2013  (NZ) .................................... 614928

(51) Int. Cl.
*A61M 15/00* (2006.01)
*A61M 11/00* (2006.01)

(52) U.S. Cl.
CPC ........ *A61M 15/008* (2014.02); *A61M 15/009* (2013.01); *A61M 15/0026* (2014.02);
(Continued)

(58) Field of Classification Search
CPC ....................... A61M 15/0068; A61M 15/008; G16H 20/10; G16H 20/13
See application file for complete search history.

(56) References Cited

U.S. PATENT DOCUMENTS 5,331,953 A * 7/1994 Andersson ............ A61M 15/00
128/200.14
5,347,998 A * 9/1994 Hodson ............. A61M 15/0091
128/200.23
(Continued)

OTHER PUBLICATIONS

International Search Report Written Opinion of the International Searching Authority issued in International Application No. PCT/NZ2014/000184.

*Primary Examiner* — Kathryn E Ditmer
(74) *Attorney, Agent, or Firm* — Kenealy Vaidya LLP

(57) ABSTRACT

Some embodiments are directed to a compliance monitor for monitoring patient usage of a medicament inhaler, the medicament inhaler including a store of medicament, a first housing for housing the store of medicament, a medicament dispenser for delivering a dose of medicament, a mouthpiece for directing the dose of medicament into the mouth of the patient, and a removable and replaceable cap for the mouthpiece. The compliance monitor includes a cap detector, such as a switch, for determining when the cap is covering the mouthpiece and/or for determining that the cap is being removed or replaced, with respect to the mouthpiece. The compliance monitor may also include a dose detector, such as a switch, for determining that a dose of medicament has been dispensed. Furthermore the cap is attached to the first housing by a tether or hinge.

18 Claims, 9 Drawing Sheets

Figure 1:
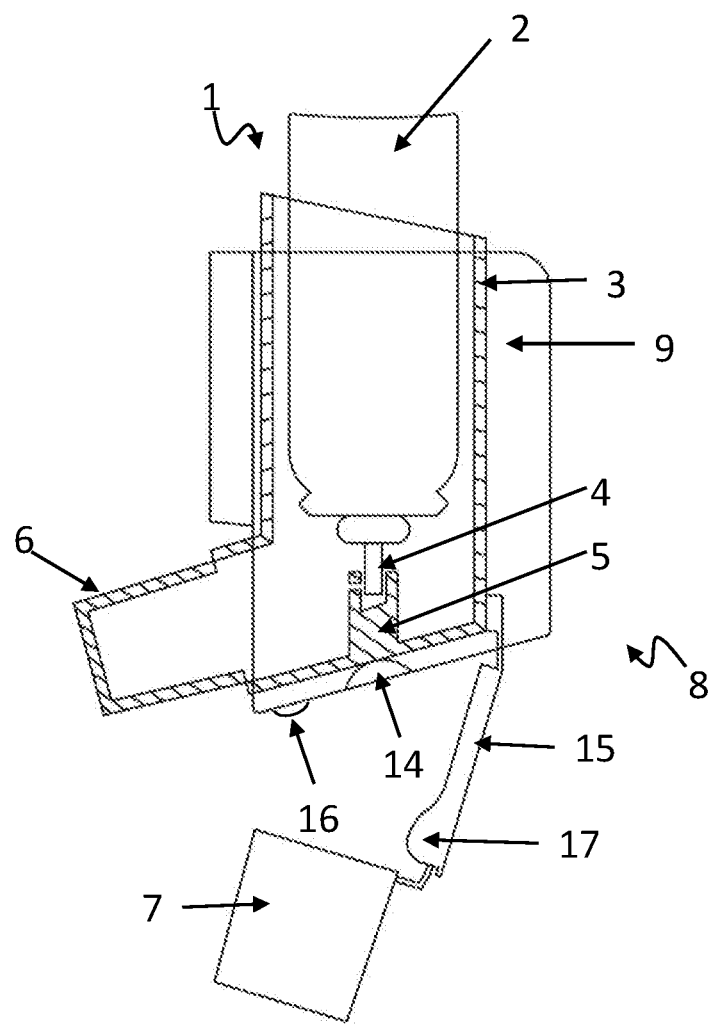

(52) U.S. Cl.
CPC ......... *A61M 11/00* (2013.01); *A61M 15/0068* (2014.02); *A61M 2205/14* (2013.01); *A61M 2205/18* (2013.01); *A61M 2205/43* (2013.01); *A61M 2205/44* (2013.01); *A61M 2205/581* (2013.01); *A61M 2205/583* (2013.01); *A61M 2205/8206* (2013.01)

(56) References Cited

U.S. PATENT DOCUMENTS

| | | | |
|---|---|---|---|
| 5,505,195 A * | 4/1996 | Wolf | A61M 15/0045 128/200.23 |
| 5,809,997 A * | 9/1998 | Wolf | A61M 15/009 128/200.23 |
| 6,076,521 A * | 6/2000 | Lindahl | A61M 15/0065 128/200.23 |
| 2002/0077369 A1 | 6/2002 | Noolandi | A61M 15/0085 424/43 |
| 2004/0069301 A1* | 4/2004 | Bacon | A61M 15/0091 128/200.23 |
| 2004/0081624 A1 | 4/2004 | Nguyen et al. | |
| 2005/0076904 A1* | 4/2005 | Jones | A61M 15/009 128/200.23 |
| 2007/0023034 A1* | 2/2007 | Jongejan | A61M 15/009 128/200.14 |
| 2007/0052544 A1* | 3/2007 | Lintell | A61J 7/0481 340/815.4 |
| 2008/0033393 A1* | 2/2008 | Edwards | A61M 5/2033 604/503 |
| 2008/0178872 A1* | 7/2008 | Genova | A61M 15/0065 128/200.23 |
| 2009/0050139 A1* | 2/2009 | Watanabe | A61M 15/0065 128/200.14 |
| 2011/0041842 A1* | 2/2011 | Bradshaw | A61M 15/0045 128/202.22 |
| 2011/0226242 A1* | 9/2011 | Von Hollen | A61M 15/009 128/203.12 |
| 2013/0151162 A1* | 6/2013 | Harris | A61M 15/00 702/19 |
| 2013/0239957 A1* | 9/2013 | Pinfold | A61M 11/04 128/200.23 |
| 2013/0269685 A1* | 10/2013 | Wachtel | A61M 15/0065 128/200.21 |
| 2015/0011906 A1* | 1/2015 | Wallach | A61K 36/00 600/538 |
| 2015/0100335 A1* | 4/2015 | Englehard | G06F 19/3462 705/2 |
| 2016/0051776 A1* | 2/2016 | Von Hollen | G06F 19/3481 128/200.23 |
| 2016/0166766 A1* | 6/2016 | Schuster | G06F 19/3468 702/54 |
| 2016/0256639 A1* | 9/2016 | Van Sickle | A61M 15/008 |

* cited by examiner

COMPLIANCE MONITOR FOR A MEDICAMENT INHALER

CROSS REFERENCE TO RELATED APPLICATION

This application is a National Phase filing under 35 C.F.R. § 371 of and claims priority to International Application No.: PCT/NZ2014/000184, filed on Aug. 29, 2014, which claims the priority benefit under 35 U.S.C. § 119 of New Zealand Application No.: 614928, filed on Aug. 30, 2013, the contents of which are hereby incorporated in their entireties by reference.

FIELD

This invention relates to a compliance monitor for a medicament inhaler, such as pressurised metered dose inhalers, dry powder inhalers, nebulisers and analgesic inhalers.

BACKGROUND

The use of medicament inhalers for the treatment of respiratory diseases such as asthma, COPD, cystic fibrosis, and bronchiectasis is well known.

A common type of medicament inhaler is what is known as a pressurised metered dose inhaler (pMDI). Such inhalers generally comprise a medicament canister and an actuator.

The medicament canister contains medicament under pressure and is designed to deliver a metered dose of medicament in the form of an aerosol spray. The actuator comprises a generally L-shaped hollow tube which has a first open end adapted to receive the medicament canister, and a second open end which acts as a mouthpiece. The mouthpiece is usually fitted with a removable cap.

Medicament canisters for use with a pMDI generally have a spray stem extending from one end which is adapted to engage with a spray-directing element housed within the actuator, and adjacent to the mouthpiece of the actuator. When the canister is pushed down into the actuator (and the cap has been removed) the spray stem and spray-directing element combine to direct a metered dose of medicament out through the mouthpiece, and into the mouth of the user (or into a spacer or other holding chamber, prior to being inhaled by the user). In order for an effective dose to be delivered, the user must suck on the mouthpiece at the same time as the dose is dispensed.

Another common type of medicament inhaler is a dry powder inhaler (DPI).

One type of DPI is generally in the form of a disc which includes a lever, and the lever, when actuated, dispenses a metered dose of medicament in the form of a dry powder into an appropriate receptacle adjacent a mouthpiece (which is usually covered by a cap when the DPI is not being used). The dry powder may then be inhaled by the user (namely, by sucking strongly on the mouthpiece of the inhaler).

Another common type of dry powder inhaler is in the form of a generally tube-shaped body, which includes an internal store of a suitable medicament; a rotatable base for dispensing a single dose of the medicament into an appropriate inhalation chamber; and a mouthpiece, through which a user may inhale the medicament that has been dispensed into the inhalation chamber. Such dry powder inhalers usually come with a removable and replaceable screw-cap, adapted to cover the mouthpiece and tube-shaped body of the inhaler, when the inhaler is not in use.

Usually, a single dose of medicament is dispensed into the inhalation chamber when the rotatable base is rotated as far as it will go in one direction, before being returned to its original starting position. This back-and-forth action only needs to be completed once (for dispensing each dose of medicament) and the user should hear a click when this action has been completed successfully.

An example of such a dry powder inhaler is the TURBUHALER® which is manufactured and marketed by AstraZeneca AB.

Another type of medicament inhaler is a nebuliser. Unlike pMDI's and DPI's, a nebuliser does not generally dispense a metered dose of medicament. Instead, nebulisers dispense medicament in the form of a mist which is inhaled into the lungs of a user. The nebuliser accomplishes this by using oxygen, compressed air or ultrasonic power to break up liquid solutions of medicament into small aerosol droplets which can be inhaled by the user via a mouthpiece. Nebulisers also often come with a removable cap for covering the mouthpiece.

A problem or difficulty associated with the use of medicament inhalers is poor medicament compliance. Many studies have shown that users frequently do not take their medicament at the predetermined or prescribed times and/or in the required amounts.

The consequences of this non-compliance are reduced disease control, lower quality of life, lost productivity, hospitalisation and avoidable deaths.

In order to address the issue of poor medicament compliance, there are now available a number of compliance monitoring devices for use with medicament inhalers.

Virtually all compliance monitoring devices incorporate dose counting means. In a general sense, dose counting means provide the simplest embodiment of a compliance monitor, as the dose count may indicate the number of medicament doses delivered and/or the number of medicament doses remaining in the medicament inhaler.

However, a limitation associated with early (mechanical) dose counters is that they were limited to just recording the number of doses only, that is, no other compliance data was gathered.

More recent electronic dose counters incorporate means to also record the date and time of the delivery of each dose of medicament, which provides more useful information, namely the user and/or a medical professional can determine if the user is taking his/her medicament at the required times and/or intervals. Examples of such dose counters can be found in U.S. Pat. No. 5,544,647 (Jewett et al), U.S. Pat. No. 6,202,642 (McKinnon et al), and NZ Patent No. 574666 (Sutherland et al).

Many electronic dose counters also include means for transmitting the compliance data gathered, either wirelessly or otherwise, to a docking station, website, cloud computing network or a personal computer (belonging to the user or a health professional). This compliance data may be transmitted in real time or at predetermined set times. Examples of patents which describe such technology are U.S. Pat. No. 6,958,691 (Anderson et al), U.S. Pat. No. 8,424,517 (Sutherland et al) and U.S. Pat. No. 8,342,172 (Levy et al).

Recording the date and time of each dose of medicament is useful information, however there are still limitations with just collecting such compliance data. Namely, a person reviewing the compliance data (eg, the user or a health professional) is not able to determine if the dose of medicament was delivered effectively, or at all. Hence, non-compliance may go unnoticed, possibly with dire consequences.

In recognition of this problem, there are now available compliance monitors for medicament inhalers that measure additional compliance data, at the same time as recording the date and time of the delivery of each dose of medicament.

For example, U.S. Pat. No. 5,363,842 (Mishelevich et al) describes a device which also monitors patient inhalation data, that is, how much air is inhaled through the medicament inhaler, and with what time course. The success or otherwise of the patient's inhalation may then be signalled back to the patient or to a health professional. Mishelevich also monitors for other patient usage or compliance data such as whether the medicament inhaler was shaken prior to use (which is standard procedure when using medicament inhalers).

U.S. Pat. No. 8,464,707 (Jongejan et al) describes a device which includes a temperature sensor attached to the mouthpiece of the inhaler, for placement in the mouth of the user prior to the dose of medicament being delivered. The temperature sensor is designed to ensure that the inhaler is being used correctly and/or properly positioned, prior to the dose of medicament being delivered.

WO 95/07723 (Wolf et al) describes a device which includes a fast response temperature thermistor for sensing the amount and duration of each dose of medicament administered.

U.S. Pat. No. 7,047,964 (Bacon) describes a device which includes an acoustic inducer adapted to detect the noise associated with the dispensing of a dose of medicament, and compare this noise to a known dose dispensing noise spectrum, and to only count a dose if a match is found.

However, a particular problem associated with the use of medicament inhalers, which has so far not been adequately addressed by the prior art, is that users often inadvertently forget to remove the cap from the mouthpiece of the inhaler prior to dispensing a dose of medicament. This is a problem mostly associated with the use of pMDI's (although it applies to other medicament inhalers also). Moreover, the user may often not realise that he/she has made this mistake and/or not realise that they did not receive the dose of medicament. This will result in the user not receiving their medicament at the designated time, and this may have dire consequences.

Moreover, some health professionals demonstrate use of a medicament inhaler with the cap on, and so many patients simply copy this erroneous technique.

And even if the user realised their mistake, the administering of another dose of medicament directly afterwards (and after removing the cap) will skew the compliance data, as two doses of medicament are recorded as having been dispensed, however the user has only received one of those doses (in the case of pMDI's).

And so being able to record compliance data relating to when the cap is removed and/or replaced, and/or when the user attempts to dispense a dose of medicament, with the cap still attached to the mouthpiece, would be very useful and important information, both for training purposes or feedback for the user, as well as for general medicament compliance data gathering purposes.

US Patent Publication No. 2010/0012120 (Herder et al) describes a device which locks the inhaler and prevents the cap being replaced upon the attainment of certain circumstances (for example, if too many doses have been dispensed or if the medicament supply has been exhausted). However, this arrangement is undesirable and/or somewhat meaningless, as the user can then no longer use the inhaler and/or receive their medicament. This would be of particular concern if the user was about to suffer an exacerbation event.

US Patent Publication No. 2004/0187869 (Bjorndal et al) describes a training device for a DPI. It includes a closure cap removably positioned over the mouthpiece, and an actuation assembly in the housing for actuating the start switch upon removal of the closure cap. Whilst Bjornal prevents the inhaler from being used with the cap on, it does not allow for compliance data to be gathered relating to how many times (or when) the user attempts to use the inhaler with the cap on—and this information would be useful for providing the user with training feedback and/or allowing a health professional to ascertain if the user has inherent difficulties with operation of the inhaler, which need to be addressed. For example, a young child or an elderly person or a person with intellectual disabilities is not likely to be aware of their mistake and/or be able to learn from it without outside intervention or feedback. Furthermore, another disadvantage associated with Bjornal is that if the user is unable to operate the inhaler (namely when the cap is on), they may become confused and/or disinclined to figure out the problem and/or take their required dose of medicament.

US Patent Publication No. 2011/0226242 (Von Hollen et al) describes a device which is adapted to emit an audible instruction upon the cap being removed, for example "shake canister". However, and as for Bjornal, Von Hollen does not allow for compliance data to be gathered relating to how many times (or when) the user attempts to use the inhaler with the cap on and/or when, and how often, the cap is removed and/or replaced.

Another problem associated with the use of medicament inhalers, which has also so far not been adequately addressed by any of the above prior art, is that users often inadvertently dispense a dose of medicament during the action of removing or replacing the cap (with respect to the mouthpiece). For example, for a pMDI the user may grab the top of the canister (the part protruding from the top of the actuator) when removing or replacing the cap, and the pressure exerted on the canister during these operations can sometimes lead to a dose of medicament inadvertently being dispensed. There is currently no way of differentiating between when a dose of medicament is dispensed during the normal dispensing of a dose of medicament, as compared to when a dose of medicament is inadvertently dispensed when the cap is being removed or replaced.

This problem may also occur when a spacer is being removed or replaced with respect to the mouthpiece of the medicament inhaler.

It may therefore also be of advantage if there was available a compliance monitor for a medicament inhaler which was able to differentiate between when a user dispenses a dose of medicament normally, as compared to when a dose of medicament is inadvertently dispensed when the cap (or spacer) is being removed and/or replaced.

OBJECT

It is an object of the present invention to provide a compliance monitor for a medicament inhaler, which goes some way towards addressing some of the aforementioned problems or difficulties, or which at the very least provides the public with a useful choice.

Definitions

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Throughout this specification, the terms "patient" or "user" or "person" or "patient usage", when used in relation to the use of a medicament inhaler, is to be understood to refer to any person that uses a medicament inhaler.

STATEMENTS OF INVENTION

According to one aspect of the present invention, there is provided a compliance monitor for monitoring patient usage of a medicament inhaler, the medicament inhaler including:
a) a store of medicament,
b) a first housing for housing the store of medicament,
c) a medicament dispensing means for delivering a dose of medicament,
d) a mouthpiece for directing the dose of medicament into the mouth of a user,
e) a removable and replaceable cap for the mouthpiece, and the compliance monitor including:
f) a cap detection means for determining when the cap is covering the mouthpiece and/or for determining that the cap is being removed or replaced, with respect to the mouthpiece.

According to another aspect of the present invention there is provided a compliance monitor, substantially as described above, wherein the compliance monitor further includes a dose detection means for determining that a dose of medicament has been dispensed.

According to another aspect of the present invention there is provided a compliance monitor, substantially as described above, wherein the dose detection means and the cap detection means enable it to be determined if the user dispenses a dose of medicament as the cap is being removed or replaced.

According to another aspect of the present invention there is provided a compliance monitor, substantially as described above, wherein the dose detection means and the cap detection means enable it to be determined if the user dispenses, or attempts to dispense, the dose of medicament when the cap is covering the mouthpiece of the medicament inhaler.

According to another aspect of the present invention there is provided a compliance monitor, substantially as described above, wherein the compliance monitor is housed within a second housing, the second housing being releasably attachable to the medicament inhaler.

The medicament inhaler may preferably be a medicament inhaler used for the treatment of respiratory diseases such as asthma, COPD, cystic fibrosis, and bronchiectasis. Examples include pressurised metered dose inhalers (pMDI's), dry powder inhalers (DPI's), and nebulisers.

It is envisaged however that the medicament inhaler could also be used for other types of medicament inhalers, for example analgesic inhalers used for the administering of an analgesic.

The medicament inhaler may preferably include a store of medicament, a first housing for housing the store of medicament, a medicament dispensing means for delivering a dose of medicament, a mouthpiece for directing the dose of medicament into the mouth of a user, and a removable and replaceable cap for the mouthpiece.

Such components of medicament inhalers will be readily apparent to those skilled in the art and it is not intended therefore to further describe these components in any great detail herein.

In the case of most pMDI's, the store of medicament is in the form of a pressurised medicament canister, and the first housing is in the form of a generally L-shaped hollow tube (actuator), which has a first open end adapted to house the medicament canister. A second open end of the actuator forms the mouthpiece. The medicament dispensing means is generally provided by a spray stem extending from the medicament canister which is adapted to engage with a spray-directing element housed within the actuator. When the canister is pushed down into the actuator, a metered dose of medicament is directed out through the mouthpiece (via a delivery channel) of the actuator and into the mouth of the user (who sucks on the mouthpiece at the same time that the medicament is dispensed). The removable and replaceable cap is adapted to close off the mouthpiece when the inhaler is not in use.

For a DPI, the store of medicament is generally housed within the main body (first housing) of the inhaler. The medicament dispensing means may be in the form of a rotatable base, or lever, for dispensing a single dose of the medicament into an appropriate inhalation chamber, from where it may be inhaled by the user via a mouthpiece. The removable and replaceable cap is adapted to close off the mouthpiece when the inhaler is not in use.

Reasons for having a cap include keeping the mouthpiece (and associated delivery channel) clean, and free from dust and grime, and also ensuring no foreign objects enter the mouthpiece, which may present a choking hazard.

The compliance monitor may preferably include a dose detection means for determining when a dose of medicament is dispensed.

There are many different types of dose detection means currently available for medicament inhalers, and they will be well known to those skilled in the art. Hence, it is not considered necessary to describe the workings of dose detection means in any great detail herein. Examples of dose detection means are included in all of the prior art documents referred to previously under the section "Background Art", and these patents are therefore incorporated into this patent specification, by reference.

Preferably, the dose detections means, as a minimum, may be able to determine that a dose of medicament has been dispensed by the medicament inhaler.

Preferably, the dose detection means may also record the date and time of the delivery of each dose of medicament.

Preferably, the compliance monitor may include a cap detection means for determining that the cap is being removed or replaced, with respect to the mouthpiece, whereby it may be determined if the user dispenses the dose of medicament as the cap is being removed or replaced.

Preferably, the cap detection means may further be able to determine when the cap is covering the mouthpiece, whereby it may be determined if the user dispenses, or attempts to dispense, the dose of medicament when the cap is covering the mouthpiece of the medicament inhaler.

In one embodiment the compliance monitor may be housed within the first housing, that is, the compliance monitor may be integrally formed with respect to the first housing of the medicament inhaler.

Preferably however, the compliance monitor may be housed within a second housing, and the second housing may preferably be releasably attachable to the medicament inhaler. In such an embodiment, the compliance monitor may be portable and/or reusable across a range of different medicament inhalers.

The second housing may be adapted to partially enclose the medicament inhaler (and/or the first housing associated with same).

Alternatively, the second housing may be adapted to fully enclose and/or encircle the medicament inhaler (and/or the first housing associated with same).

Examples of suitable second housings may be found our NZ Patent No. 574666 (Sutherland et al), NZ Patent No. 595367 (Sutherland et al) and U.S. Pat. No. 8,424,517 (Sutherland et al). These patents are therefore incorporated into this specification by reference.

Preferably, the compliance monitor may further include an electronics control module (ECM), the ECM being in electronic communication with the dose detection means and/or the cap detection means. Such ECM's will be familiar to those skilled in the art of compliance monitoring technology for medicament inhalers, and again examples may be found in most of the prior art referred to previously.

Preferably, the ECM may be adapted to monitor and/or manipulate and/or store and/or transmit compliance data relating to patient usage of the medicament inhaler, including all compliance data gathered by the dose detection means and/or the cap detection means.

Preferably, all such compliance data gathered by the dose detection means and the cap detection means is sent to the ECM, which then determines if the user has dispensed the dose of medicament as the cap is being removed or replaced.

Preferably, all such compliance data gathered by the dose detection means and the cap detection means is sent to the ECM, which then determines if the user has dispensed the dose of medicament when the cap is covering the mouthpiece of the medicament inhaler.

The compliance data gathered by the ECM, and/or any operations performed on the data by any component of the ECM, may be stored within a data storage area (for example, a computer memory facility) associated with the ECM.

The ECM may also include any other features which are also commonly associated with known ECM's. For example, the ECM may include a power management system (such as a battery—rechargeable or otherwise), and a user interface (such as a LCD screen with operator buttons).

Furthermore, the ECM may include, or be in communication with, a transmission means for transmitting the compliance data, or the results of any operations performed on the compliance data by the ECM, to a remote location such as a website, cloud computing site, or a personal computer (for example, belonging to the user or a health professional). This data may be transmitted in real time, manually or at predetermined set times.

The person receiving the compliance data from the ECM may then be able to review the patient's use of the medicament inhaler and be alerted to any matters of interest or concern.

For example, a health professional may be alerted if the user frequently dispenses a dose of medicament as the cap is being removed or replaced and/or if the user frequently dispenses, or attempts to dispense, a dose of medicament when the cap is covering the mouthpiece of the medicament inhaler. The health professional may then contact the user to discuss these findings and perhaps offer advice or show techniques as to how the incorrect use may be avoided or corrected (and perhaps also emphasise the possibly dire consequences of such incorrect use).

In one embodiment the ECM may be housed within the first housing, that is, the ECM may be integrally formed with respect to the first housing and/or the medicament inhaler.

Preferably however, the ECM may be housed within the second housing.

Preferably, the compliance monitor may include indication means to alert the user if the ECM determines that the user has dispensed the dose of medicament as the cap is being removed or replaced and/or if the user has dispensed the dose of medicament with the cap covering the mouthpiece of the medicament inhaler.

Any suitable indication means may be utilised. For example, the indications means may be in the form of a visual and/or audio and/or audio-visual indicator. Such indicators may comprise part of, or be operatively connected to, the compliance monitor (or the first or second housings).

For example, LED lights may flash and/or a small speaker may emit an audible warning noise or a voice recording.

In one embodiment, the cap may be attached to the first housing of the medicament inhaler by a tether.

In an alternative embodiment, the cap may be attached to the second housing by a tether.

Having the cap tethered in such a fashion ensures that the cap is not inadvertently dropped or lost once it has been removed from the mouthpiece. Furthermore, having a tethered cap ensures that the cap does not become a choking hazard.

Preferably, the cap detection means may include a switch, and this switch may be actuated (or de-actuated) by the tether during the action of removing and replacing the cap, respectively.

In other embodiments, the cap detection means, such as a switch, may be located on the compliance monitor, and the cap detection means may be actuated (or de-actuated) by the action of removing and/or replacing the cap with respect to the compliance monitor and/or with respect to the medicament inhaler—to which the compliance monitor is attached.

In alternative embodiments, the cap detect switch may be opened or closed by the movement of the medicament inhaler base held within the compliance monitor resulting from the replacement or removal of the cap onto the mouthpiece of the medicament inhaler.

The switch may preferably be an electronic or electromechanical switch, although any type of switch is within the scope of this invention.

In one embodiment, the switch may be located on the first housing.

In an alternative embodiment, the switch may be located on the second housing.

In either embodiment, the action of removing and/or replacing the cap may result in an actuation (or de-actuation) of the switch (by the tether), and an appropriate electrical signal may be sent to the ECM. If at the same time the user inadvertently triggers the medicament dispensing means, the dose detection means will detect this and also send an appropriate electrical signal to the ECM. The ECM will, upon receiving both signals, more or less simultaneously, be able to determine that a dose of medicament has not in fact been dispensed (to the user) and that instead a user error has occurred, and this determination may be stored and/or transmitted, as described previously. Alternatively and/or additionally, the user may be alerted to the error by the indication means.

Preferably, the switch may also be (continuously) actuated by the tether when the cap is covering the mouthpiece. Hence, an appropriate signal may be continually sent to the ECM indicating that the cap is attached to the mouthpiece. If the user dispenses, or attempts to dispense, a dose of medicament whilst the cap is attached to the mouthpiece, the dose detecting means will detect this and send a signal to the ECM. The ECM, will thus be able to determine that the dose was dispensed with the cap attached, and this determination may be stored and/or transmitted, and/or indicated to the user, as described previously.

In such a fashion, compliance data relating to two common user errors of medicament inhalers may be collected, stored and/or used to provide feedback to the user regarding their techniques and/or provide further training in the use of the medicament inhaler.

Furthermore, either the user or a health care professional may be alerted to the fact that the user has not taken their medicament, even though a dose has been dispensed. This is an important consideration for a user who thought that they did in fact take their medicament (in the situation where the cap is left on during the administering of a dose of medicament), and so that person can be alerted to take another dose (with the cap off). Hence, as well as ensuring proper medicament compliance generally, this invention may also potentially prevent an exacerbation event.

According to a further aspect of the present invention, there is provided a compliance monitor for monitoring patient usage of a medicament inhaler, substantially as described above, wherein the compliance monitor further includes a spacer detection means for determining that a spacer is being removed or replaced, with respect to the mouthpiece, whereby it may be determined if the user dispenses the dose of medicament as the spacer is being removed or replaced.

In such an embodiment, the invention will work substantially the same as described previously (in relation to when the cap is being removed or replaced), the only difference being that the compliance monitor also (or alternatively) detects if the medicament inhaler inadvertently dispenses a dose when a spacer is being removed or replaced.

According to another aspect of the present invention, there is provided a compliance monitor for monitoring patient usage of a dry powder medicament delivery device, the medicament delivery device including:
a) a store of medicament housed within a main body portion,
b) a base portion, said base portion and said main body portion being rotatable with respect to each other,
c) a medicament dispensing means for dispensing a dose of the medicament into an inhalation chamber,
d) a mouthpiece through which the dose of medicament may be inhaled by a user,
e) a removable and replaceable cap,
and the compliance monitor including:
f) a first portion for receiving and/or retaining the base portion of the medicament delivery device,
g) a second portion for releasably securing the medicament delivery device to the first portion, thereby releasably attaching the compliance monitor to the medicament delivery device,
the arrangement and construction being such that the fitting of the second portion of the compliance monitor to the first portion of the compliance monitor includes a screw fit.

Preferred Embodiments

The description of a preferred form of the invention to be provided herein, with reference to the accompanying drawings, is given purely by way of example and is not to be taken in any way as limiting the scope or extent of the invention.

DRAWINGS

Figure 2:
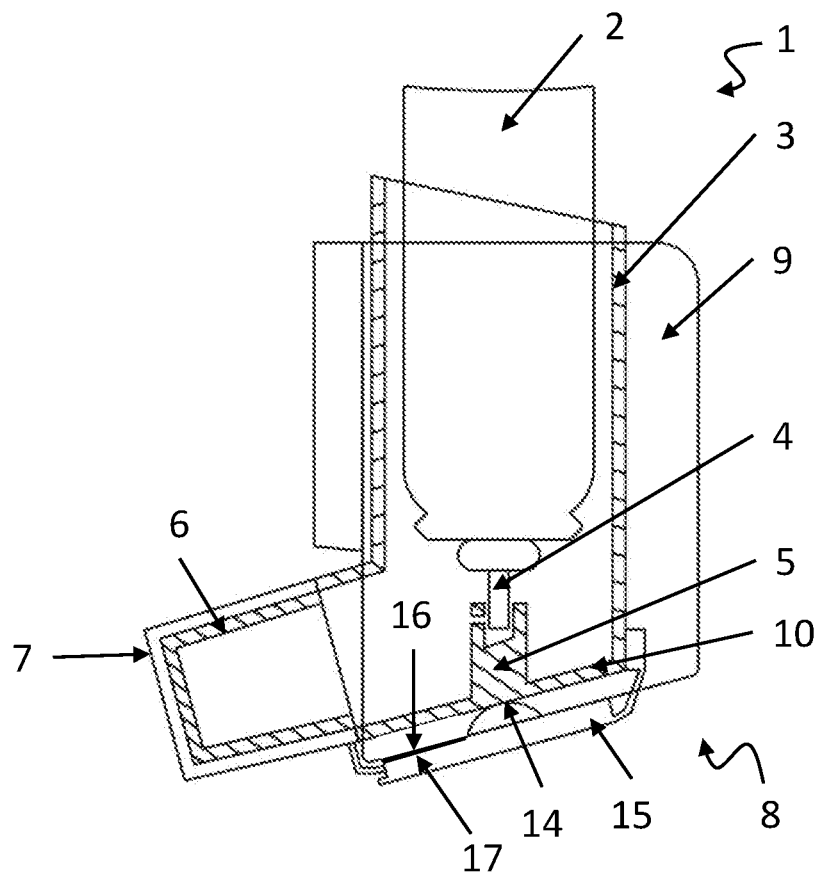
Figure 3:
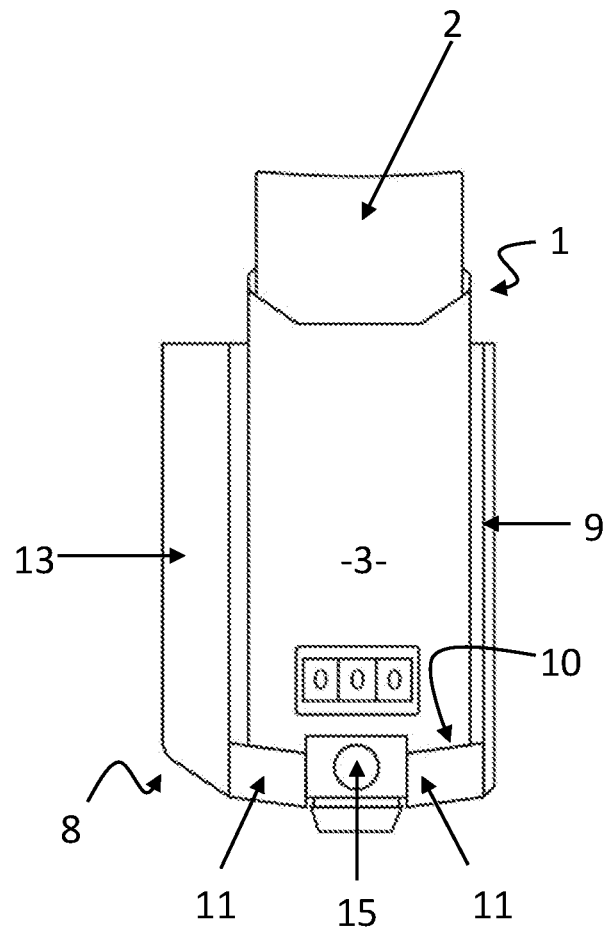
Figure 4:
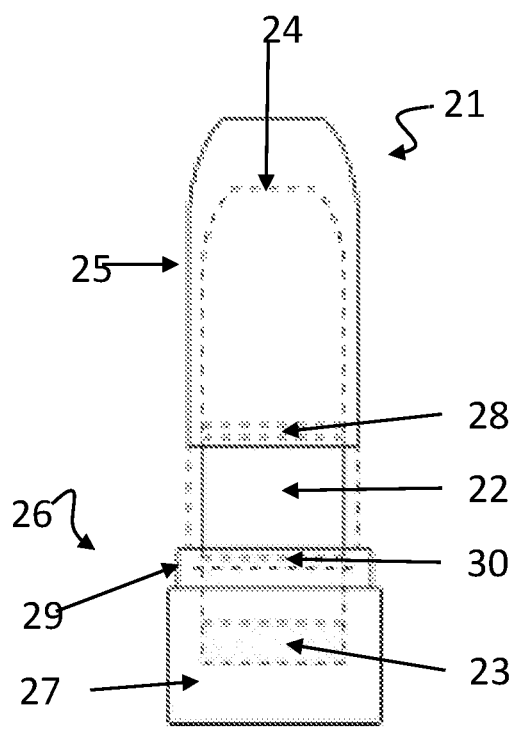
Figure 5:
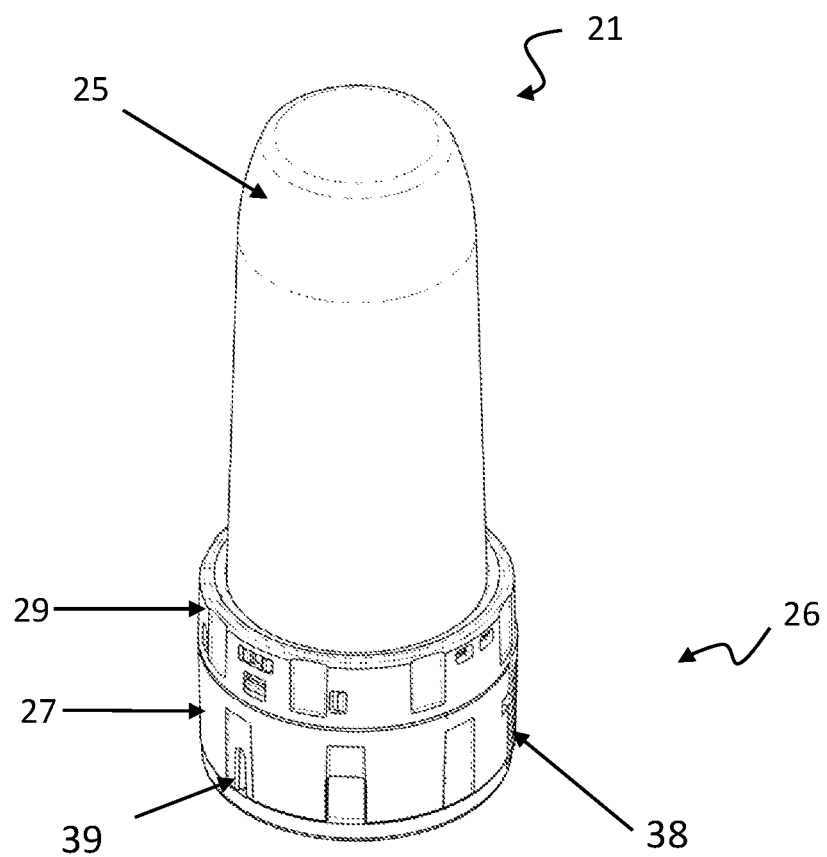
Figure 6:
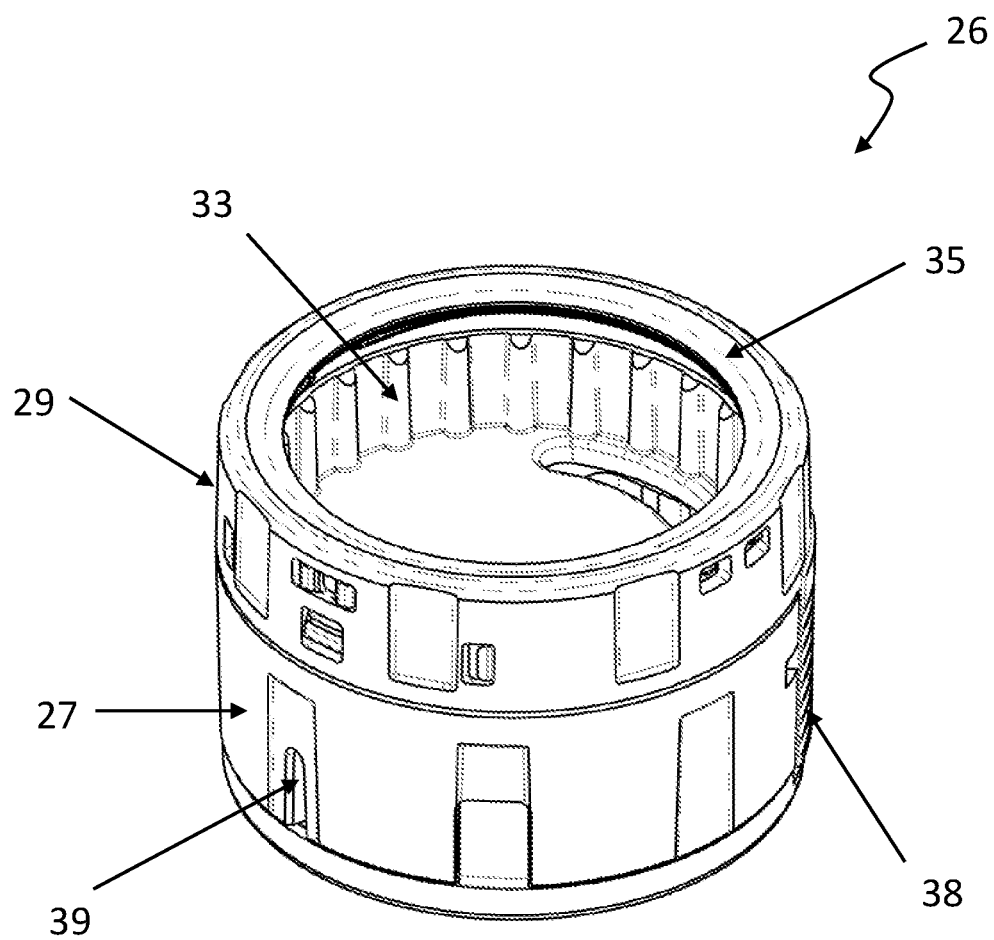
Figure 7:
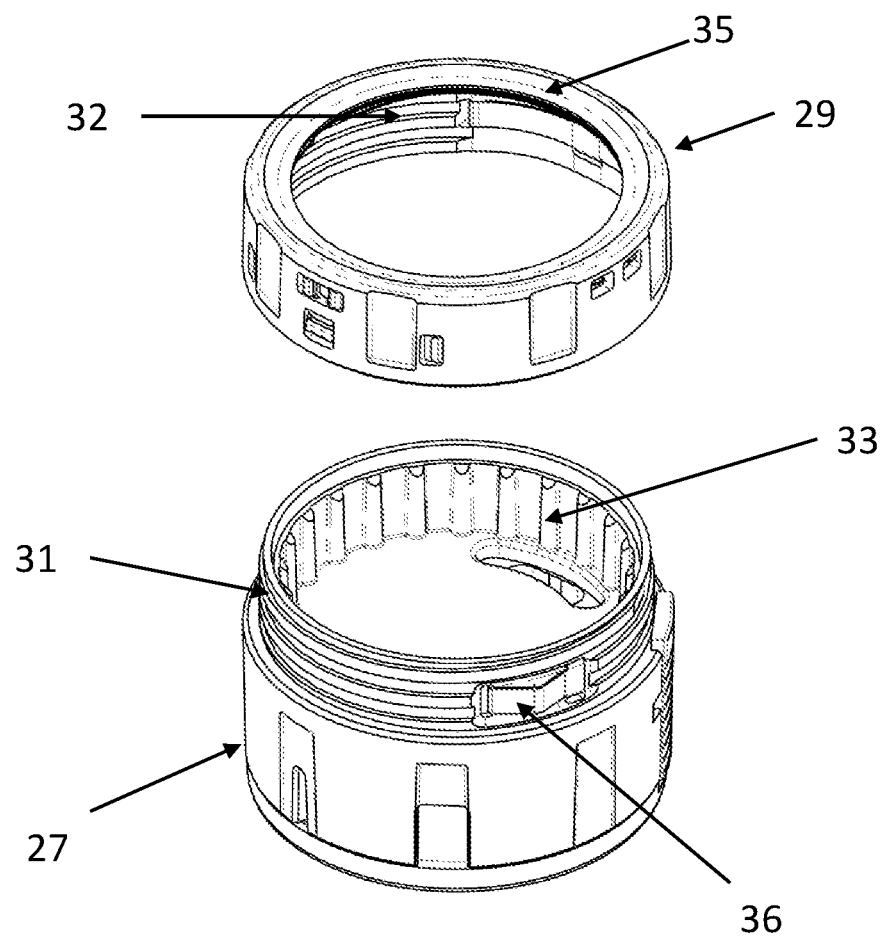
Figure 8:
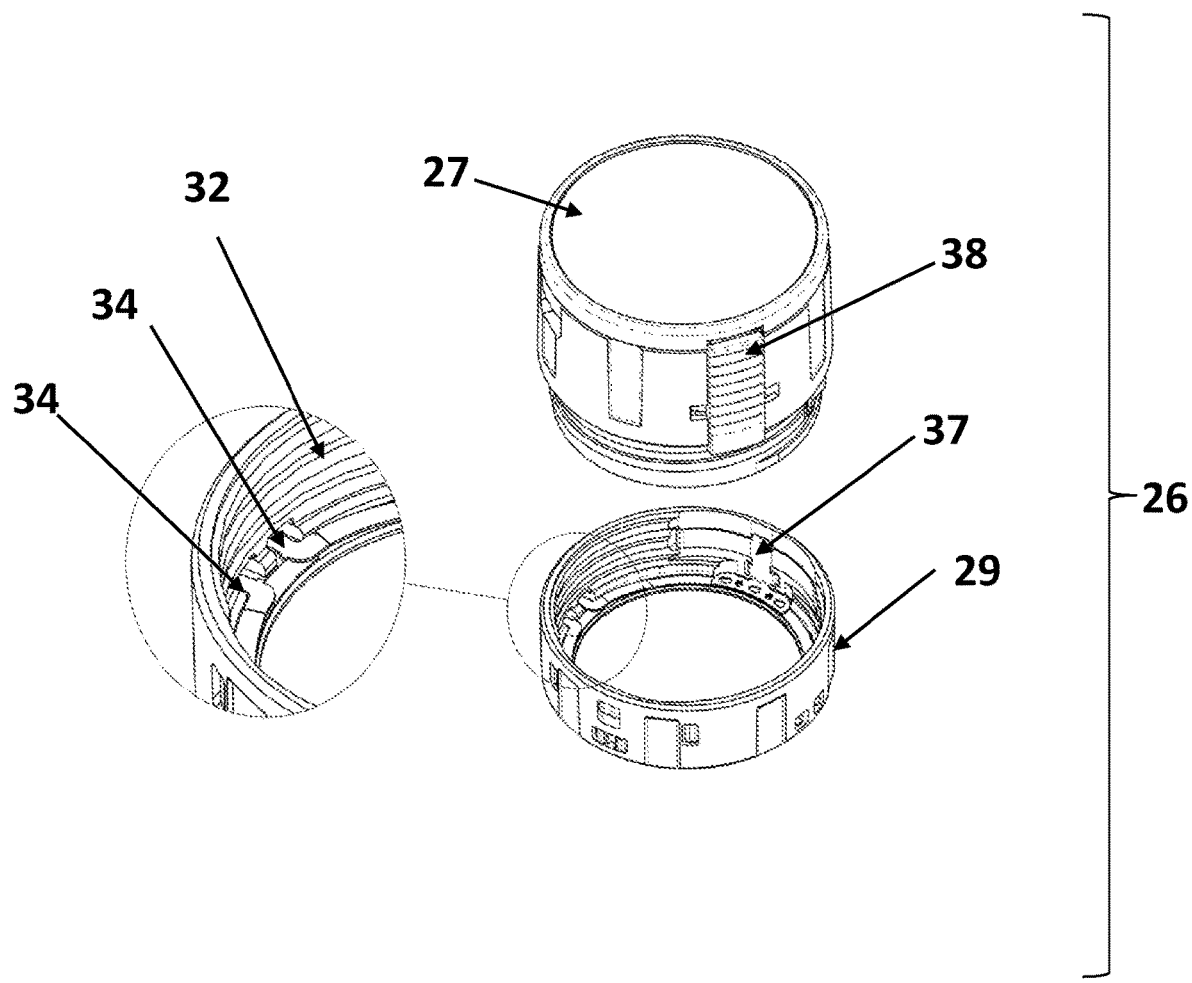
Figure 9:
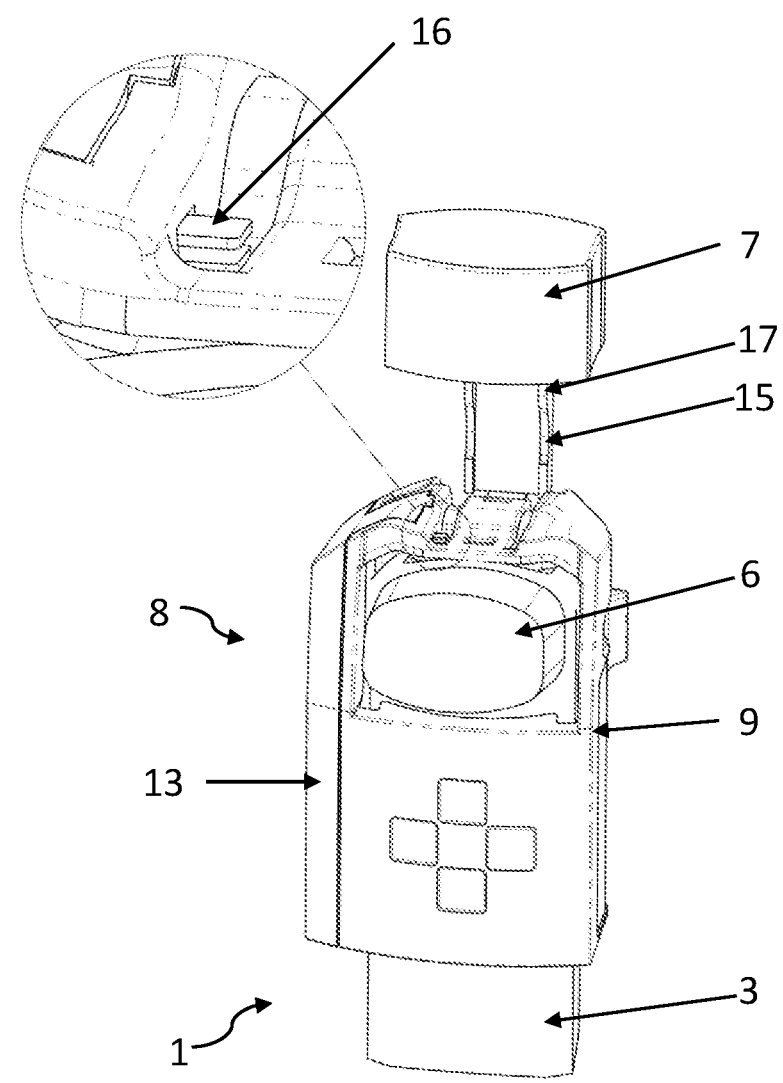

FIG. 1: is a cut-away side view showing one possible embodiment of the invention, with the cap removed from the mouthpiece of a pMDI medicament inhaler, FIG. 2: is a view of the embodiment illustrated in FIG. 1, with the cap attached to the mouthpiece of the pMDI medicament inhaler, FIG. 3: is a rear view of the embodiments illustrated in FIGS. 1 & 2, FIG. 4: is a view of another possible embodiment of the present invention, when applied to a TURBUHALER® DPI, FIG. 5: is a perspective view of another possible embodiment of the present invention, when applied to a TURBUHALER® DPI, FIG. 6: is a perspective view of the compliance monitor illustrated in FIG. 5, FIG. 7: is an exploded view of the compliance monitor illustrated in FIG. 6, FIG. 8: is an inverted perspective view of the exploded view illustrated in FIG. 7, and FIG. 9: is an inverted perspective front view of the compliance monitor illustrated in FIGS. 1 to 3.

DESCRIPTION OF PREFERRED EMBODIMENTS

Having regard to FIGS. 1 and 2 there is shown a pMDI medicament inhaler, generally indicated by arrow 1.

The medicament inhaler 1 includes a store of medicament in the form of a pressurised medicament canister 2, and a first housing (for housing the canister 2) in the form of an actuator 3.

The inhaler 1 is also provided with a medicament dispensing means for delivering a dose of medicament. The medicament dispensing means is in the form of a spray stem 4 extending from the canister 2, which is adapted to engage with a spray-directing element 5 housed within the actuator 3. When the canister 2 is pushed down into the actuator 3, the spray stem 4 and spray-directing element 5 combine to deliver a metered dose of medicament out through the mouthpiece 6 of the actuator 3, and into the mouth of the user (who sucks on the mouthpiece 6 at the same time that the medicament is dispensed).

The inhaler 1 is also provided with a removable and replaceable cap 7, which is adapted to close off the mouthpiece 6 when the inhaler 1 is not in use.

The cap 7 ensures that the mouthpiece 6 remains clean, and free from dust and grime, and also ensures that no foreign objects (such as coins) can enter the mouthpiece 6 (for example when the inhaler is not in use or being carried in a pocket or purse), which may otherwise present a choking hazard.

The cap 7 is attached to the rear of the actuator 3 by a tether 15. Having the cap 7 tethered to the actuator 3 in such a fashion ensures that the cap 7 is not inadvertently dropped or lost once it has been removed. Furthermore, having a tethered cap 7 ensures that the cap 7 does not become a choking hazard (that is, the cap 7 could not inadvertently be swallowed by a user because it is attached to the actuator 3, via the tether 15).

The inhaler 1 also includes a compliance monitor, generally indicated by arrow 8.

The compliance monitor 8 is housed within a second housing 9, which is releasably attachable to the inhaler 1 (or more specifically to the actuator 3).

As may be best seen in FIG. 3, the second housing 9 only partially encloses the inhaler 1. That is, the second housing 9 encloses the sides and front of the inhaler 1, however the rear of the second housing 9 is left open. This rear opening allows for the inhaler 1 to be placed into, and removed from, the second housing 9. When the inhaler 1 is placed into the second housing 9, the bottom 10 of the actuator housing 3 rests on the ledges 11 formed along the bottom sides of the second housing 9.

The compliance monitor 8 includes an ECM (not shown, but see FIG. 3) which is included within one side 13 of the second housing 9.

The ECM is adapted to monitor and/or manipulate and/or store and/or transmit compliance data relating to patient usage of the inhaler 1.

Because the second housing 9 is releasably attachable to the inhaler 1, it may be appreciated that the compliance monitor 8 may be portable and/or reusable across a range of different medicament inhalers.

The compliance monitor 8 includes a dose detection means in the form of a first electromechanical switch 14, which is in electronic communication with the ECM. The first switch 14 is located on a lower internal surface of the second housing 9, and the first switch 14 therefore abuts the bottom 10 of the actuator 2.

When a dose of medicament is dispensed, the canister 2 is pushed down into the actuator 3, as described previously. This pressure forces the bottom 10 of the actuator 3 against the first switch 14, which closes (or actuates) the first switch 14, and thus the dispensing of the dose is detected, and an appropriate signal is sent to the ECM, where the dispensing of the dose is recorded, and the date and time of the dispensing of the dose is also recorded. Such a dose detecting apparatus has been previously described in our patent application WO2013/043063, which is incorporated herein, in its entirety, by reference.

The compliance monitor 8 also includes a cap detection means.

The cap detection means includes a second switch 16 located on the underside of the lower surface of the second housing 9 (that is, the underside of the compliance monitor 8). Further, the tether 15 includes a protrusion 17 which is adapted to butt up against, and therefore actuate (or de-actuate), the second switch 16 during the action of removing and replacing the cap 7 (with respect to the mouthpiece 6 of the inhaler 1).

Hence, the action of removing and/or replacing the cap 7 results in an actuation (or de-actuation) of the second switch 16 (by the protrusion 17 of the tether 15), and an appropriate electrical signal is sent to the ECM.

If, at the same time as removing or replacing the cap 7, the user inadvertently dispenses a dose of medicament, the cap detection means and the dose detection means (second switch 16 and first switch 14 respectively) will combine to detect this, and appropriate electrical signals will be sent to the ECM. The ECM will, upon receiving both signals (more or less simultaneously) be able to determine that a dose of medicament has not in fact been dispensed to the user, and that instead a user error has occurred, and this determination may be stored and/or transmitted, as described previously.

Furthermore, (and as illustrated in FIG. 2) the protrusion 17 of the tether 15 is adapted to butt up against, and therefore continually actuate, the second switch 16 when the cap 7 is covering the mouthpiece 6 of the inhaler 1.

Hence, an appropriate electrical signal may be continually sent to the ECM indicating that the cap 7 is attached to the mouthpiece 6. If the user dispenses, or attempts to dispense, a dose of medicament whilst the cap 7 is attached to the mouthpiece 6, the cap detection means and the dose detection means (second switch 16 and first switch 14 respectively) will combine to detect this, and appropriate electrical signals will be sent to the ECM. The ECM, will thus be able to determine that the dose was dispensed (or attempted to be dispensed) with the cap 7 attached, and this determination may be stored and/or transmitted, as described previously.

Alternatively, and/or additionally, the user may be alerted to either of the above two errors by an indication means, substantially as described previously (indication means not shown in the drawings).

In such a fashion, it may be appreciated that compliance data relating to two common user errors of medicament inhalers may be collected, stored and/or used to provide feedback to the user regarding their techniques, and/or prompt a health professional to provide or schedule further training for the user in relation to their use of the medicament inhaler 1.

Furthermore, either the user or a health care professional may be alerted to the fact that the user has not taken their medicament, even though a dose has been dispensed. This is an important consideration for a user who thought that they did in fact take their medicament (in the situation where the cap 7 is left on during the administering of a dose of medicament), and so that person can be alerted to take another dose (with the cap 7 removed). Hence, as well as ensuring proper medicament compliance generally, the compliance monitor 8 may also potentially prevent an exacerbation event.

It is fairly common for users to either inadvertently leave the cap 7 on when administering a dose of medicament and/or inadvertently dispense a dose of medicament when removing or replacing the cap 7, and these type of errors have potentially adverse consequences. For example, the patient may become ill or incapacitated (or worse) as a result of not having received their medicament at the required time.

Furthermore, a health care professional upon reviewing skewed compliance data (that is, data supplied by an inhaler that does not utilise the compliance monitor 8) may change the dosage regime that the user is currently on, without realising that not as many doses of medicament have been taken as was thought. This scenario is clearly undesirable, and the compliance monitor 8 therefore serves as a very useful and important tool to address these type of issues.

Having regard to FIGS. 4 to 8, there is shown further possible embodiments of the present invention. FIGS. 4 to 8 illustrate medicament inhalers in the form of TURBU-HALER® DPI inhalers, generally indicated by arrow 21.

Having regard to FIG. 4, the inhaler 21 includes a store of medicament in the form of a dry powder (not shown) housed within a first (circular) housing 22. The inhaler 21 includes a medicament dispensing means in the form of a rotatable base 23. A metered dose of medicament is dispensed into a dispensing chamber (not shown) by rotating the base 23 back and forth once. The inhaler 21 also includes a mouthpiece 24 and the medicament is inhaled by the user via the mouthpiece 24. The internal workings of the inhaler 21 assist is forcing the medicament out of the dispensing chamber, and into the mouth of the user.

The inhaler 21 is also provided with a removable and replaceable (circular) cap 25, which is adapted to close off the mouthpiece 24, and also serves to close off (or enclose) the first housing 22 when the inhaler 21 is not in use.

The inside surface of the lower portion of the cap 25 contains a thread 28 (shown in dotted outline).

The inhaler 21 also includes a compliance monitor, generally indicated by arrow 26.

The compliance monitor 26 includes a dose detection means housed within a releasably attachable second housing 27. The second housing 27 is releasably attachable to the bottom of the first housing 22, and is fixed with respect to the rotatable base 23. The action of rotating the rotatable base 23 back and forth once (to release a dose of medicament) is detected by the dose detection means, and the dispensing of a dose is therefore recorded and an electrical signal is sent to the ECM (ECM not shown, but it is also housed within the second housing 27)

The compliance monitor 26 also includes a cap detection means.

The cap detection means includes a circular sleeve 29, which is adapted to sit directly above the second housing 27, and is connected and/or retained thereto by a screw fit (not shown in FIG. 4). In FIG. 4 only, the inside surface of the upper portion of the circular sleeve 29 contains a thread 30 (shown in dotted outline), which is complimentary to the thread 28, whereby the cap 25 may be screwed into the circular sleeve 29, to thereby securely retain the cap 25 with respect to the circular sleeve 29 (and thereby retain the cap 25 with respect to the inhaler 21 and/or second housing 27).

In FIG. 4, the action of screwing the cap 25 into the circular sleeve 29 has the effect of closing two electrical contacts (not shown), and when these contacts are closed, an electrical signal is sent to the ECM to indicate that the cap is attached to the inhaler 21. Likewise, when the cap 25 is unscrewed from the circular sleeve 29, the electrical contacts are opened, and an appropriate signal is again sent to the ECM to indicate that the cap has been removed from the inhaler 21.

If the ECM receives a signal that a dose of medicament has been dispensed at substantially the same time that that cap 25 has been removed, it can be determined that the dose has been inadvertently dispensed during the removal of the cap 25. Likewise, if the ECM receives a signal that a dose of medicament has been dispensed with the cap 25 still secured to the inhaler 21, the ECM can determine this. Furthermore if doses of medicament are continually dispensed with the cap 25 remaining on, it can be determined that the user has not been taking their medicament.

Hence, a person reviewing such compliance data can be alerted to these incorrect techniques and the user can thus be alerted, with possibly a view to further training in the use of the inhaler 21.

Having regard to FIGS. 5 to 8, the cap detection means includes the circular sleeve 29, which is adapted to sit directly above the second housing 27, and is connected and/or retained thereto by a screw fit.

The outside top portion of the second housing 27 contains a thread 31 which is complimentary to the thread 32 of the inside lower surface of the circular sleeve 29. Once the base of the inhaler 21 is placed in the grip portion 33 of the second housing 27, the circular sleeve 29 can be screwed onto the second housing 27 thereby securing the compliance monitor 26 to the inhaler 21.

In FIGS. 5 to 8, the cap 25 is screwed onto the base of the inhaler (rather than being screwed into the circular sleeve 29—as per FIG. 4).

When the inhaler 21 is fitted into the compliance monitor 26 without the cap 25, spring switches 34 are left open. When the cap 25 is fitted onto the inhaler 21 and screwed onto it tightly, the base of the inhaler 21 is pulled up towards the rim 35 of the circular sleeve 29 and the spring switches 34 are therefore closed.

The compliance monitor 26 further includes a PCB contact switch 36 on the top outer portion of the second housing 27 which engages with contact point 37 on the inside of the circular sleeve 29 to detect that the parts are fitted together.

The compliance monitor 26 may also include a latch 38 which secures the circular sleeve 29 and second housing 27 together, until the latch 38 is released before the parts are unscrewed.

The compliance monitor 26 may further include a LED light 39, for example to indicate that the parts 27 and 29 are properly attached and/or to indicate that the compliance monitor 26 has been properly attached to the inhaler 21.

Having regard to FIG. 9, there is shown an inverted perspective front view of the compliance monitor 8 illustrated in FIGS. 1 to 3.

In FIG. 9, the switch 16, which is part of the cap detection means, is shown in greater detail on the underside of the second housing 9.

As previously mentioned, the tether 15 includes a protrusion 17 which is adapted to butt up against, and therefore actuate (or de-actuate), the switch 16 during the action of removing and replacing the cap 7 (with respect to the mouthpiece 6 of the inhaler 1). Hence, the action of removing and/or replacing the cap 7 results in an actuation (or de-actuation) of the switch 16 (by the protrusion 17 of the tether 15), and an appropriate electrical signal is sent to the ECM.

Furthermore, the protrusion 17 of the tether 15 is adapted to butt up against, and therefore continually actuate, the switch 16 when the cap 7 is continuously covering the mouthpiece 6 of the inhaler 1.

VARIATIONS

While the embodiments described above are currently preferred, it will be appreciated that a wide range of other variations might also be made within the general spirit and scope of the invention and/or as defined by the appended claims.

I claim:

1. A compliance monitor for monitoring patient usage of a medicament inhaler, the medicament inhaler including:
   (a) a store of medicament,
   (b) a first housing for housing the store of medicament,
   (c) a medicament dispenser for delivering a dose of medicament,
   (d) a mouthpiece for directing the dose of medicament into the mouth of the patient,
   (e) a removable and replaceable cap for the mouthpiece, and the compliance monitor comprising:
   (f) a cap detector configured to perform at least one of:
      determining when the cap is covering the mouthpiece, and
      determining that the cap is being removed or replaced, with respect to the mouthpiece,
   (g) a dose detector configured to determine that a dose of medicament has been dispensed,
      wherein the compliance monitor is housed within a second housing,
      wherein the second housing is releasably attachable to the medicament inhaler, and
      wherein the compliance monitor is configured to determine when the user dispenses a dose of medicament as the cap is being removed or replaced based on data from the dose detector and the cap detector.

2. The compliance monitor as claimed in claim 1, wherein the compliance monitor is configured to determine when the user dispenses, or attempts to dispense, the dose of medicament when the cap is covering the mouthpiece of the medicament inhaler based on data from the dose detector and the cap detector.

3. The compliance monitor as claimed in claim 1, wherein the compliance monitor further includes an electronics control module (ECM), the ECM being in electronic communication with the dose detector and the cap detector.

4. The compliance monitor as claimed in claim 3, wherein the ECM is configured to monitor and/or manipulate and/or store and/or transmit data relating to patient usage of the medicament inhaler.

5. The compliance monitor as claimed in claim 1, wherein the cap is attached to the first housing of the medicament inhaler by a tether.

6. The compliance monitor as claimed in claim 5, wherein the cap detector includes a switch, and this switch is configured to be actuated, or de-actuated, by the tether during the action of removing or replacing the cap.

7. The compliance monitor as claimed in claim 6, wherein the switch is located on the first housing.

8. The compliance monitor as claimed in claim 6, wherein the switch is located on the second housing.

9. The compliance monitor as claimed in claim 5, wherein the cap detector includes a switch, and this switch is configured to be actuated by the tether when the cap is covering the mouthpiece.

10. The compliance monitor as claimed in claim 1, wherein the cap is attached to the second housing by a tether.

11. The compliance monitor as claimed in claim 1, wherein the second housing is adapted to partially enclose the medicament inhaler.

12. The compliance monitor as claimed in claim 1, wherein the second housing is adapted to full enclose and/or encircle the medicament inhaler.

13. The compliance monitor as claimed in claim 1, wherein the compliance monitor further includes a spacer detector configured to determine that a spacer is being removed from or replaced on the medicament inhaler and the compliance monitor is configured to determine when the user dispenses the dose of medicament as the spacer is being removed or replaced.

14. The compliance monitor as claimed in claim 1, the second housing comprising:
   a) a first portion for receiving and/or retaining a base portion of the medicament inhaler,
   b) a second portion for releasably securing the medicament inhaler to the first portion, thereby releasably attaching the compliance monitor to the medicament inhaler,
   the arrangement and construction being such that a fitting of the second portion of the second housing to the first portion of the second housing includes:
   a screw fit.

15. A compliance monitor for monitoring patient usage of a medicament inhaler, the medicament inhaler including:
   (a) a store of medicament,
   (b) a first housing for housing the store of medicament,
   (c) a medicament dispenser for delivering a dose of medicament,
   (d) a mouthpiece for directing the dose of medicament into the mouth of the patient,
   (e) a removable and replaceable cap for the mouthpiece, and the compliance monitor comprising:
   (f) a cap detector configured to perform at least one of:
      determining when the cap is covering the mouthpiece, and
      determining that the cap is being removed or replaced, with respect to the mouthpiece,
   (g) a dose detector configured to determine that a dose of medicament has been dispensed,
      wherein the compliance monitor is housed within a second housing,
      wherein the second housing is releasably attachable to the medicament inhaler, and
      wherein data gathered by the dose detector and the cap detector is configured to be sent to an ECM, which is configured to determine if the user has dispensed the dose of medicament as the cap is being removed or replaced based on the data.

16. A compliance monitor for monitoring patient usage of a medicament inhaler, the medicament inhaler including:
   (a) a store of medicament,
   (b) a first housing for housing the store of medicament,
   (c) a medicament dispenser for delivering a dose of medicament,
   (d) a mouthpiece for directing the dose of medicament into the mouth of the patient,
   (e) a removable and replaceable cap for the mouthpiece, and the compliance monitor comprising:
   (f) a cap detector configured to perform at least one of:
      determining when the cap is covering the mouthpiece, and
      determining that the cap is being removed or replaced, with respect to the mouthpiece,
   (g) a dose detector configured to determine that a dose of medicament has been dispensed,
      wherein the compliance monitor is housed within a second housing,
      wherein the second housing is releasably attachable to the medicament inhaler, and
      wherein data gathered by the dose detector and the cap detector is configured to be sent to an ECM, which is configured to determine if the user has dispensed, or attempted to dispense, the dose of medicament when the cap is covering the mouthpiece of the medicament inhaler based on the data.

17. The compliance monitor as claimed in claim 15 or claim 16, wherein the compliance monitor further includes an indicator configured to alert the user if the ECM determines that: (a) with regard to claim 15, the user has dispensed the dose of medicament as the cap is being removed or replaced or (b) with regard to claim 16, if the user has dispensed, or attempted to dispense, the dose of medicament when the cap is covering the mouthpiece of the medicament inhaler.

18. The compliance monitor as claimed in claim 17, wherein the indicator is in the form of a visual and/or audio and/or audio-visual indicator.

* * * * *